US011324829B2

(12) United States Patent
Fujisawa et al.

(10) Patent No.: US 11,324,829 B2
(45) Date of Patent: May 10, 2022

(54) ANTISEPTIC AGENT COMPRISING MEGLUMINE OR SALT THEREOF

(71) Applicant: Santen Pharmaceutical Co., Ltd., Osaka (JP)

(72) Inventors: Toyomi Fujisawa, Nara (JP); Koji Sakanaka, Nara (JP); Shinya Umezaki, Nara (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 289 days.

(21) Appl. No.: 16/074,267

(22) PCT Filed: Mar. 13, 2017

(86) PCT No.: PCT/JP2017/009875
§ 371 (c)(1),
(2) Date: Jul. 31, 2018

(87) PCT Pub. No.: WO2017/159585
PCT Pub. Date: Sep. 21, 2017

(65) Prior Publication Data
US 2020/0147222 A1  May 14, 2020

(30) Foreign Application Priority Data
Mar. 14, 2016 (JP) .............................. JP2016-050091

(51) Int. Cl.
*A61K 47/26* (2006.01)
*A61K 9/00* (2006.01)
*A61K 9/08* (2006.01)
*A61K 47/18* (2017.01)

(52) U.S. Cl.
CPC ............ *A61K 47/26* (2013.01); *A61K 47/183* (2013.01); *A61K 9/0048* (2013.01); *A61K 9/08* (2013.01)

(58) Field of Classification Search
None
See application file for complete search history.

(56) References Cited

U.S. PATENT DOCUMENTS

| 8,945,543 | B2 * | 2/2015 | Igawa | ..................... A61P 37/02 424/130.1 |
|---|---|---|---|---|
| 2002/0016317 | A1 * | 2/2002 | Schul | ..................... A23L 25/10 514/182 |
| 2003/0119825 | A1 | 6/2003 | Folger et al. | |
| 2008/0207629 | A1 | 8/2008 | Folger et al. | |
| 2008/0242707 | A1 * | 10/2008 | Schuckler | .......... A61K 31/4412 514/350 |
| 2009/0117097 | A1 | 5/2009 | Igawa et al. | |
| 2011/0124682 | A1 | 5/2011 | Sumida et al. | |
| 2012/0034319 | A1 | 2/2012 | Gupta et al. | |
| 2012/0065186 | A1 * | 3/2012 | Li | .......................... A61K 47/40 514/210.21 |
| 2015/0125532 | A1 * | 5/2015 | Manning | ................. A61P 17/00 424/489 |

FOREIGN PATENT DOCUMENTS

| JP | 2008222674 A | 9/2008 | |
|---|---|---|---|
| JP | 2010508372 A | 3/2010 | |
| JP | 2011524854 A | 9/2011 | |
| KR | 10-2009-0084925 A | 8/2009 | |
| KR | 10-2011-0027786 A | 3/2011 | |
| TW | 200302720 A | 8/2003 | |
| WO | 2004082673 A1 | 9/2004 | |
| WO | 2006132363 A1 | 12/2006 | |
| WO | 2008/055871 A1 | 5/2008 | |
| WO | 2009/154304 A1 | 12/2009 | |
| WO | 2010/056872 A2 | 5/2010 | |
| WO | 2014051163 A1 | 4/2014 | |
| WO | WO-2014184631 A1 * | 11/2014 | ........... A61K 9/2013 |

OTHER PUBLICATIONS

Chromy et al. Clin. Chem 24/2, pp. 379-38 (Year: 1978).*
Capsule Sizes [online]. Capsule Connection available online from Feb. 5, 2015 [retrieved on Aug. 11, 2021]. Retrieved from the internet: <https://web.archive.org/web/20150205002941/http://capsuleconnection.com/capsule-sizing-info>. (Year: 2015).*
Official Action dated Apr. 2, 2020, by the Russian Federal Service for Intellectual Property in Russian Patent Application No. 2018135980 and an English translation of the Action. (21 pages).
International Search Report (PCT/ISA/210) dated Apr. 18, 2017, by the Japanese Patent Office as the International Searching Authority for International Application No. PCT/JP2017/009875.
Written Opinion (PCT/ISA/237) dated Apr. 18, 2017, by the Japanese Patent Office as the International Searching Authority for International Application No. PCT/JP2017/009875.
Pashirova, Tatiana N., et al. , "Self-assembling systems based on quaternized derivatives of 1,4-diazabicyclo[2.2.2]octane in nutrient broth as antimicrobial agents and carriers for hydrophobic drugs", Colloids and Surfaces B: Biointerfaces 2015, 127, pp. 266-273.
Zhulenko V.N., Gorshkov G.I. Pharmacology. M.: KolosS, 2008, pp. 34-35.
Official Action dated Aug. 18, 2020, by the Russian Patent Office in corresponding Russian Patent Application No. 2018135980, and an English translation of the Action. (14 pages).

(Continued)

*Primary Examiner* — Katherine Peebles
(74) *Attorney, Agent, or Firm* — Buchanan Ingersoll & Rooney PC

(57) ABSTRACT

The present invention addresses the problem of providing a novel application of meglumine or a salt thereof. The present invention is an antiseptic agent consisting of meglumine or a salt thereof, and a pharmaceutical composition comprising the antiseptic agent according to the present invention, and pertaining to: a pharmaceutical composition which does not comprise benzalkonium chloride and which is placed in a reusable container; a product that comprises the pharmaceutical composition comprising the antiseptic agent according to the present invention and a reusable container; and a method of improving the antiseptic effect of the pharmaceutical composition by comprising meglumine or a salt thereof in the pharmaceutical composition that has been placed in the reusable container.

3 Claims, No Drawings

(56) References Cited

OTHER PUBLICATIONS

Office Action dated Dec. 1, 2020, by the Taiwanese Patent Office in corresponding Taiwanese Patent Application No. 106108102. (5 pages).
Office Action dated Feb. 9, 2021, by the Japanese Patent Office in corresponding Japanese Patent Application No. 2017-047062. (4 pages).
Office Action dated Feb. 9, 2021, by the Korean Patent Office in corresponding Korean Patent Application No. 10-2018-728896. (11 pages).
Nybond et al., "Antimicrobial assay optimization and validation for HTS in 384-well format using a bioluminescent *E. coli* K-12 strain," European Journal of Pharmaceutical Sciences, 2013, vol. 49, pp. 782-789 and Supplementary, pp. 1-7.
Rode et al., "Responses of *Staphylococcus aureus* exposed to HCl and organic acid stress," Canadian Journal of Microbiology, 2010, vol. 56, No. 9, pp. 777-792. (cited in Office Action dated Mar. 15, 2022, by the Korean Patent Office in corresponding KR Patent Application No. 10-2018-7028896).

\* cited by examiner

ANTISEPTIC AGENT COMPRISING MEGLUMINE OR SALT THEREOF

TECHNICAL FIELD

The present invention relates to an antiseptic agent consisting of meglumine or a salt thereof.

BACKGROUND ART

Meglumine, which is a type of amino sugar, is used as a pharmaceutical additive such as a stabilizer, a buffer agent, and a pH regulator. Meglumine amidotrizoate, a salt of meglumine, is used as an active ingredient of an X-ray contrast medium, and meglumine gadopentetate is used as an active ingredient of an MRI contrast medium.

Patent Document 1 describes a composition comprising meglumine and a microbicide PHMB (polyhexamethylene biguanide), in which meglumine supplementarily improves the microbicidal effect of the microbicide. Patent Document 2 describes a composition comprising meglumine, rebamipide, and boric acid, and Patent Document 3 describes a composition comprising meglumine, rebamipide, boric acid, and zinc chloride. Such compositions are also documented to show an antiseptic effect or an antimicrobial activity. Further, Nonpatent Document 1 describes that meglumine enhances the antimicrobial activity of N-hexadecanyl-1,4-diazabicyclo[2.2.2]octane (hereinafter may also be referred to as N-hexadecanyl-DABCO) which is abbreviated as mono-CS.

Patent Document 1: Pamphlet of PCT International Publication No. WO2004/082673
Patent Document 2: U.S. Published Patent Application Publication, No. 2011/0124682, Specification
Patent Document 3: Pamphlet of PCT International Publication No. WO2014/051163
Non-Patent Document 1: Colloids and Surfaces, B: Biointerfaces 2015, 127, 266-273

DISCLOSURE OF THE INVENTION

Problems to be Solved by the Invention

However until now, it has not been known that meglumine alone has an antiseptic effect.

An object of the present invention is to provide a new use of meglumine.

Means for Solving the Problems

Surprisingly, the present inventors found that a composition containing meglumine can show a sufficient antiseptic effect even in the absence of an antiseptic agent. Then the present invention has been completed. Specifically, the present invention can provide the followings.

(1) An antiseptic agent consisting of meglumine or a salt thereof.
(2) The antiseptic agent according to (1), which is for use in a pharmaceutical composition to be placed in a repeatedly operable container.
(3) The antiseptic agent according to (1) or (2), which is for use in a pharmaceutical composition not comprising benzalkonium chloride.
(4) The antiseptic agent according to any one of (1) to (3), which is for use in a pharmaceutical composition not comprising polyhexamethylene biguanide.
(5) The antiseptic agent according to any one of (1) to (4), which is for use in a pharmaceutical composition not comprising boric acid or a salt thereof.
(6) The antiseptic agent according to any one of (1) to (5), which is for use in a pharmaceutical composition not comprising N-hexadecanyl-DABCO.
(7) The antiseptic agent according to any one of (1) to (6), which is for use in a pharmaceutical composition comprising 0.0001 to 0.1% (w/v) of edetic acid or a salt thereof.
(8) An antiseptic composition comprising the antiseptic agent according to any one of (1) to (7), but not comprising an antiseptic agent other than the antiseptic agent according to any one of (1) to (7).
(9) A pharmaceutical composition comprising the antiseptic agent according to any one of (1) to (7), the pharmaceutical composition not comprising benzalkonium chloride, polyhexamethylene biguanide, or N-hexadecanyl-DABCO, and
the pharmaceutical composition having a content of boric acid or a salt thereof of less than 0.03% (w/v) (comprising 0) and being placed in a repeatedly operable container.
(10) A pharmaceutical composition comprising the antiseptic agent according to any one of (1) to (7), the pharmaceutical composition comprising no or a predetermined amount of an antiseptic agent other than the antiseptic agent according to any one of (1) to (7),
the predetermined amount being such that a common logarithmic value of the ratio (B/A) of a cell count (B) to a cell count (A) is 3.3 or less, the cell count (A) being a viable cell count as measured by inoculating and uniformly mixing a test sample consisting of the antiseptic agent other than the antiseptic agent according to any one of (1) to (7) and water with *Escherichia coli* ATCC 8739 at a microorganism liquid concentration within a range of between $10^5$ and $10^6$ cfu/mL, storing the test sample at 20 to 25° C. under a light shielding condition for 14 days, and then withdrawing 1 mL of the test sample with a micropipette to measure the viable cell count, and the cell count (B) being at the time of the inoculation, and
the pharmaceutical composition having a content of boric acid or a salt thereof of less than 0.03% (w/v) (comprising 0) and being placed in a repeatedly operable container.
(11) The pharmaceutical composition according to (9) or (10), having a content of meglumine or a salt thereof of 0.1 to 20% (w/v).
(12) The pharmaceutical composition according to any one of (9) to (11), having a pH of 4.0 to 9.5.
(13) A product comprising the pharmaceutical composition according to any one of (9) to (12), and a repeatedly operable container.
(14) A method of improving an antiseptic effect of a pharmaceutical composition, the method comprising further comprising meglumine or a salt thereof in the pharmaceutical composition, the pharmaceutical composition not comprising benzalkonium chloride, polyhexamethylene biguanide, or N-hexadecanyl-DABCO, and
the pharmaceutical composition having a content of boric acid or a salt thereof of less than 0.03% (w/v) (comprising 0) and being placed in a repeatedly operable container.
(15) A method of improving an antiseptic effect of a pharmaceutical composition, the method comprising meglumine or a salt thereof in the pharmaceutical composition, the pharmaceutical composition comprising no or a predetermined amount of an antiseptic agent,
the predetermined amount being such that a common logarithmic value of the ratio (B/A) of a cell count (B) to a cell count (A) is 3.3 or less, the cell count (A) being a viable cell count as measured by inoculating and uniformly mixing a test sample consisting of the antiseptic agent and water with *Escherichia coli* ATCC 8739 at a microorganism liquid concentration within a range of between $10^5$ and $10^6$ cfu/mL, storing the test sample at 20 to 25° C. under a light shielding condition for 14 days, and then withdrawing 1 mL of the test sample with a micropipette to measure the viable cell count, and the cell count (B) being at the time of the inoculation, and the pharmaceutical composition having a content of boric acid or a salt thereof of less than 0.03% (w/v) (comprising 0).

(16) A method of improving an antiseptic effect of a pharmaceutical composition, the method comprising further comprising meglumine or a salt thereof in the pharmaceutical composition, the pharmaceutical composition being placed in a repeatedly operable container, and the pharmaceutical composition before adding meglumine or a salt thereof having a common logarithmic value of the ratio (B/A) of a cell count (B) to a cell count (A) of 3.3 or less, the cell count (A) being a viable cell count as measured by inoculating and uniformly mixing the pharmaceutical composition with *Escherichia coli* ATCC 8739 at a microorganism liquid concentration within a range of between $10^5$ and $10^6$ cfu/mL, storing the pharmaceutical composition at 20 to 25° C. under a light shielding condition for 14 days, and then withdrawing 1 mL of the pharmaceutical composition with a micropipette to measure the viable cell count, and the cell count (B) being at the time of the inoculation.

It is noted that any two or more of the embodiments according to (1) to (15) may be selected and combined.

Effects of the Invention

An embodiment of the present invention can provide an antiseptic agent consisting of meglumine or a salt thereof. Further, an embodiment of the present invention can provide a novel pharmaceutical composition comprising meglumine or a salt thereof, the pharmaceutical composition showing a sufficient antiseptic effect even when a container thereof is subjected to repetitive opening and closing operations.

PREFERRED MODE FOR CARRYING OUT THE INVENTION

Below, the present invention will be described in detail.
<Antiseptic Agent>

Meglumine for constituting the antiseptic agent according to an embodiment of the present invention is a compound represented by the following formula (1), which is also called N-methyl glucamine, 1-deoxy-methylamino-D-glucitol, and the like.
[Formula 1]

Meglumine for constituting the antiseptic agent according to an embodiment of the present invention may be in a form of a salt, and there is no particular limitation for the salt as long as it is pharmaceutically acceptable. Examples of the salt comprise salts of inorganic acids, salts of organic acids, quaternary ammonium salts, salts of halogen ions, salts of alkali metals, salts of alkaline earth metals, metal salts, salts of organic amines, and the like. Salts of inorganic acids comprise salts of hydrochloric acid, hydrobromic acid, hydroiodic acid, nitric acid, sulfuric acid, phosphoric acid, and the like. Salts of organic acids comprise salts of acetic acid, oxalic acid, fumaric acid, maleic acid, succinic acid, malic acid, citric acid, tartaric acid, adipic acid, gluconic acid, glucohept acid, glucuronic acid, terephthalic acid, methanesulfonic acid, alanine, lactic acid, hippuric acid, 1,2-ethanedisulfonic acid, isethionic acid, lactobionic acid, oleic acid, gallic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid, sulfosalicylic acid, and the like. Quaternary ammonium salts comprise salts of methyl bromide, methyl iodide, and the like. Salts of halogen ions comprise salts of chloride ions, bromide ions, iodide ions, and the like. Salts of alkali metals comprise salts of lithium, sodium, potassium, and the like. Salts of alkaline earth metals comprise salts of calcium, magnesium, and the like. Metal salts comprise salts of iron, zinc, and the like. Salts of organic amines comprise salts of triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, N,N-bis(phenylmethyl)-1,2-ethanediamine, and the like.

Meglumine or a salt thereof for constituting the antiseptic agent according to an embodiment of the present invention may be in a form of a hydrate or solvate.

The antiseptic agent according to an embodiment of the present invention may be used for a pharmaceutical composition. The antiseptic agent according to an embodiment of the present invention alone has an antiseptic effect. Therefore, it may be suitably used for a pharmaceutical composition comprising a pharmaceutical composition which does not contain any antiseptic agent other than the antiseptic agent according to an embodiment of the present invention. For example, the antiseptic agent according to an embodiment of the present invention may be used for a pharmaceutical composition which does not contain benzalkonium chloride, a pharmaceutical composition which does not contain polyhexamethylene biguanide, a pharmaceutical composition which does not contain boric acid or a salt thereof, a pharmaceutical composition which does not contain a quaternary ammonium salt other than benzalkonium chloride, a pharmaceutical composition which does not contain N-hexadecanyl-DABCO, and the like.
<Antiseptic Composition>

The present invention encompasses the aforementioned antiseptic agent (meglumine or a salt thereof) and antiseptic compositions which do not contain an antiseptic agent other than the antiseptic agent according to an embodiment of the present invention. The antiseptic composition in an embodiment of the present invention may also comprise any component (except for antiseptic agents other than meglumine or a salt thereof), and for example, may be combined with an additive described below in the <pharmaceutical composition> section (for example, a surfactant, a buffer agent, a tonicity agent, a stabilizing agent, an anti-oxidative agent, a high molecular weight polymer, a pH adjuster, and the like) and/or a solvent (water, alcohol, and the like) to form one antiseptic composition which does not contain an antiseptic agent other than the antiseptic agent according to an embodiment of the present invention (meglumine or a salt thereof).
<Pharmaceutical Composition>

The pharmaceutical composition according to an embodiment of the present invention contains the aforementioned antiseptic agent according to an embodiment of the present invention.

There is no particular limitation for the content of meglumine or a salt thereof in a pharmaceutical composition comprising the antiseptic agent according to an embodiment of the present invention as long as it is enough to obtain the desired antiseptic effect, but it is preferably 0.1 to 20% (w/v), more preferably 0.2 to 15% (w/v), still more preferably 0.3 to 10% (w/v), yet more preferably 0.4 to 8% (w/v), in particular preferably 0.5 to 6% (w/v), and most preferably 1 to 5% (w/v). It is noted that when a salt of meglumine is contained in a pharmaceutical composition comprising the antiseptic agent according to an embodiment of the present invention, these values correspond to the contents in terms of free meglumine. It is noted that the term "% (w/v)" means a mass (g) of a target component (in this case, meglumine) contained in 100 mL of the pharmaceutical composition according to an embodiment of the present invention. The same applies below unless otherwise stated.

The antiseptic agent according to an embodiment of the present invention may be used in combination of another antiseptic agent in order to obtain a better antiseptic effect. The phrase "used in combination" means that the antiseptic agent according to an embodiment of the present invention and another antiseptic agent is contained in one pharmaceutical composition. Examples of another antiseptic agent comprise benzalkonium chloride, benzalkonium bromide, benzethonium chloride, benzododecinium bromide, sorbic acid, potassium sorbate, methyl parahydroxybenzoate, propyl parahydroxybenzoate, chlorobutanol, chlorhexidine, boric acid or a salt thereof, edetic acid or a salt thereof, and the like. Examples of a salt of boric acid comprise borax, sodium borate, potassium borate, and the like. Examples of a salt of edetic acid comprise monosodium edetate, disodium edetate, tetrasodium edetate, sodium citrate, and the like. Disodium edetate is preferred, and disodium edetate dihydrate is particularly preferred. There is no particular limitation for the content of another antiseptic agent to be used in combination in a pharmaceutical composition comprising the antiseptic agent according to an embodiment of the present invention as long as, for example, it is enough to obtain the desired antiseptic effect, but it is preferably 0.00001 to 5% (w/v), more preferably 0.00005 to 3% (w/v), still more preferably 0.0001 to 2% (w/v), yet more preferably 0.0005 to 1.5% (w/v), and in particular preferably 0.0007 to 1% (w/v). In the case of boric acid and a salt thereof, the content thereof in total is preferably 0.0001 to 5% (w/v), more preferably 0.0005 to 3% (w/v), still more preferably 0.001 to 2% (w/v), yet more preferably 0.005 to 1.5% (w/v), even more preferably 0.01 to 1% (w/v), in particular preferably 0.05 to 0.8% (w/v), and most preferably 0.1 to 0.6% (w/v). It is noted that when a salt of boric acid is contained in the pharmaceutical composition according to an embodiment of the present invention, these values correspond to the contents in terms of free boric acid. In the case of edetic acid or a salt thereof, the content thereof in total is preferably 0.00001 to 0.5% (w/v), more preferably 0.00005 to 0.3% (w/v), still more preferably 0.0001 to 0.1% (w/v), yet more preferably 0.0005 to 0.08% (w/v), even more preferably 0.001 to 0.07% (w/v), in particular preferably 0.005 to 0.06% (w/v), and most preferably 0.007 to 0.05% (w/v). It is noted that when a salt of edetic acid or a hydrate thereof is contained in the pharmaceutical composition according to an embodiment of the present invention, these values correspond to the contents calculated based on the mass of the salt of edetic acid or the hydrate thereof.

The antiseptic agent according to an embodiment of the present invention may be used in combination with another antiseptic agent as described above, but the pharmaceutical composition according to an embodiment of the present invention may comprise no or a predetermined amount of an antiseptic agent other than the antiseptic agent according to an embodiment of the present invention because the aforementioned antiseptic agent (meglumine or a salt thereof) according to an embodiment of the present invention alone can show a sufficient antiseptic effect. Here, the term "predetermined amount" refers to, for example, an amount at which an antiseptic effect is not obtained when used alone. Specifically, the common logarithmic value of the ratio (B/A) of a cell count (B) to a cell count (A) is preferably 3.3 or less, more preferably 3.0 or less, still more preferably 2.8 or less, in particular preferably 2.5 or less, and most preferably 2.0 or less, the cell count (A) being a viable cell count as measured by inoculating and uniformly mixing a test sample consisting of an antiseptic agent and water with *Escherichia coli* ATCC 8739 at a microorganism liquid concentration within a range of between $10^5$ and $10^6$ cfu/mL, storing the test sample at 20 to 25° C. under a light shielding condition for 14 days, and then withdrawing 1 mL of the test sample with a micropipette to measure the viable cell count, and the cell count (B) being at the time of the inoculation. The "predetermined amount" may vary depending on the type of an antiseptic agent, but, for example, it is preferably 0.001% (w/v) or less, more preferably 0.0007% (w/v) or less, still more preferably 0.0005% (w/v) or less, yet more preferably 0.0003% (w/v) or less, and in particular preferably 0.0001% (w/v) or less. Most preferably an antiseptic agent is not substantially contained.

In particular the pharmaceutical composition according to an embodiment of the present invention preferably comprises no or a small amount of benzalkonium chloride as an antiseptic agent. When benzalkonium chloride is comprised in the pharmaceutical composition according to an embodiment of the present invention, it is preferably comprised in a predetermined amount. Here, the term "predetermined amount" refers to, for example, an amount at which an antiseptic effect is not obtained when used alone. Specifically, the common logarithmic value of the ratio (B/A) of a cell count (B) to a cell count (A) is preferably 3.3 or less, more preferably 3.0 or less, still more preferably 2.8 or less, in particular preferably 2.5 or less, and most preferably 2.0 or less, the cell count (A) being a viable cell count as measured by inoculating and uniformly mixing a test sample consisting of an antiseptic agent and water with *Escherichia coli* ATCC 8739 at a microorganism liquid concentration within a range of between $10^5$ and $10^6$ cfu/mL, storing the test sample at 20 to 25° C. under a light shielding condition for 14 days, and then withdrawing 1 mL of the test sample with a micropipette to measure the viable cell count, and the cell count (B) being at the time of the inoculation. More specifically, the "predetermined amount" of benzalkonium chloride is preferably 0.001% (w/v) or less, more preferably 0.0007% (w/v) or less, still more preferably 0.0005% (w/v) or less, yet more preferably 0.0003% (w/v) or less, and in particular preferably 0.0001% (w/v) or less. Most preferably benzalkonium chloride is not substantially contained. Further, the pharmaceutical composition according to an embodiment of the present invention preferably comprises no or a small amount of a quaternary ammonium salt used as an antiseptic agent other than benzalkonium chloride. Examples of the quaternary ammonium salt other than benzalkonium chloride comprise benzalkonium bromide, benzethonium chloride, benzododecinium bromide, N-hexadecanyl-DABCO, and the like. When a quaternary ammonium salt other than benzalkonium chloride is comprised in the pharmaceutical composition according to an embodiment of the present invention, it is preferably comprised in a predetermined amount. Here, the term "predetermined amount" refers to, for example, an amount at which an antiseptic effect is not obtained when used alone. Specifically, the common logarithmic value of the ratio (B/A) of a cell count (B) to a cell count (A) is preferably 3.3 or less, more preferably 3.0 or less, still more preferably 2.8 or less, in particular preferably 2.5 or less, and most preferably 2.0 or less, the cell count (A) being a viable cell count as measured by inoculating and uniformly mixing a test sample consisting of an antiseptic agent (a quaternary ammonium salt other than benzalkonium chloride) and water with *Escherichia coli* ATCC 8739 at a microorganism liquid concentration within a range of between $10^5$ and $10^6$ cfu/mL, storing the test sample at 20 to 25° C. under a light shielding condition for 14 days, and then withdrawing 1 mL of the test sample with a micropipette to measure the viable cell count, and the cell count (B) being at the time of the inoculation. The "predetermined amount" may vary depending on the type of a quaternary ammonium salt, but, for example, a quaternary ammonium salt other than benzalkonium chloride is preferably not comprised in an amount of no less than 0.01% (w/v) (the content is less than 0.01% (w/v)), more preferably not comprised in an amount of no less than 0.005% (w/v), still more preferably not comprised in an amount of no less than 0.001% (w/v), yet more preferably not comprised in an amount of no less than 0.0005% (w/v), and in particular preferably not comprised in an amount of no less than 0.0001% (w/v). Most preferably it is not substantially comprised. Moreover, in particular when an antiseptic agent other than a quaternary ammonium salt is N-hexadecanyl-DABCO, N-hexadecanyl-DABCO is preferably not comprised in an amount of no less than 0.5% (w/v) (the content is less than 0.5% (w/v)), more preferably not comprised in an amount of no less than 0.10% (w/v) (the content is less than 0.10% (w/v)), still more preferably not comprised in an amount of no less than 0.05% (w/v), yet more preferably not comprised in an amount of no less than 0.01% (w/v), yet still more preferably not comprised in an amount of no less than 0.005% (w/v), even more preferably not comprised in an amount of no less than 0.001% (w/v), and in particular preferably not comprised in an amount of no less than 0.0005% (w/v). Most preferably it is not substantially comprised.

Preferably, the pharmaceutical composition according to an embodiment of the present invention also comprises no or a small amount of an antiseptic agent other than a quaternary ammonium salt. Antiseptic agents other than a quaternary ammonium salt comprise sorbic acid, potassium sorbate, methyl parahydroxybenzoate, propyl parahydroxybenzoate, chlorobutanol, chlorhexidine, polyhexamethylene biguanide, boric acid or a salt thereof, edetic acid or a salt thereof, and the like. When an antiseptic agent other than a quaternary ammonium salt is comprised in the pharmaceutical composition according to an embodiment of the present invention, it is preferably comprised in a predetermined amount. Here, the term "predetermined amount" refers to, for example, an amount at which an antiseptic effect is not obtained when used alone. Specifically, the common logarithmic value of the ratio (B/A) of a cell count (B) to a cell count (A) is preferably 3.3 or less, more preferably 3.0 or less, still more preferably 2.8 or less, in particular preferably 2.5 or less, and most preferably 2.0 or less, the cell count (A) being a viable cell count as measured by inoculating and uniformly mixing a test sample consisting of the above antiseptic agent (an antiseptic agent other than a quaternary ammonium salt) and water with *Escherichia coli* ATCC 8739 at a microorganism liquid concentration within a range of between $10^5$ and $10^6$ cfu/mL, storing the test sample at 20 to 25° C. under a light shielding condition for 14 days, and then withdrawing 1 mL of the test sample with a micropipette to measure the viable cell count, and the cell count (B) being at the time of the inoculation. The "predetermined amount" may vary depending on the type of an antiseptic agent other than a quaternary ammonium salt, but, for example, an antiseptic agent other than a quaternary ammonium salt is preferably not comprised in an amount of no less than 0.5% (w/v) (the content is less than 0.5% (w/v)), more preferably not comprised in an amount of no less than 0.10% (w/v) (the content is less than 0.10% (w/v)), still more preferably not comprised in an amount of no less than 0.05% (w/v), yet more preferably not comprised in an amount of no less than 0.01% (w/v), yet still more preferably not comprised in an amount of no less than 0.005% (w/v), and in particular preferably not comprised in an amount of no less than 0.001% (w/v). Most preferably it is not substantially comprised. In particular, when the antiseptic agent other than a quaternary ammonium salt is boric acid or a salt thereof, boric acid and a salt thereof are preferably not comprised in an amount of no less than 0.5% (w/v) (the content is less than 0.5% (w/v)), more preferably not comprised in an amount of no less than 0.10% (w/v) (the content is less than 0.10% (w/v)), still more preferably not comprised in an amount of no less than 0.05% (w/v), yet more preferably not comprised in an amount of no less than 0.03% (w/v), yet still more preferably not comprised in an amount of no less than 0.01% (w/v), even more preferably not comprised in an amount of no less than 0.005% (w/v), and in particular preferably not comprised in an amount of no less than 0.001% (w/v). Most preferably they are not substantially comprised. Examples of a salt of boric acid comprise borax, sodium borate, potassium borate, and the like. It is noted that when a salt of boric acid is contained in the pharmaceutical composition according to an embodiment of the present invention, these values correspond to the contents in terms of free boric acid. Further, edetic acid or a salt thereof, which is often added to a pharmaceutical composition as a stabilizing agent, is also known to have an antiseptic effect. When edetic acid or a salt thereof is comprised in the pharmaceutical composition according to an embodiment of the present invention, the content thereof in total is more than 0% (w/v) (0.0001% or more, 0.0005% or more, 0.001% or more, 0.002% or more, 0.003% or more, 0.005% or more, 0.007% or more, and the like), but preferably 0.5% (w/v) or less, more preferably 0.3% (w/v) or less, even more preferably 0.1% (w/v) or less, still more preferably 0.08% (w/v) or less, yet still more preferably 0.05% (w/v) or less, further more preferably 0.03% (w/v) or less, in particular preferably 0.01% (w/v) or less, and most preferably 0.005% (w/v) or less. Examples of a salt of edetic acid comprise monosodium edetate, disodium edetate, tetrasodium edetate, sodium citrate, and the like. Disodium edetate is preferred, and disodium edetate dihydrate is particularly preferred. In particular, the pharmaceutical composition according to an embodiment of the present invention does not preferably comprise an antiseptic agent other than edetic acid and a salt thereof. It is noted that when a salt of edetic acid or a hydrate thereof is contained in the pharmaceutical composition according to an embodiment of the present invention, these values correspond to the contents calculated based on the mass of a salt of edetic acid or a hydrate thereof. Further, in particular when the antiseptic agent other than a quaternary ammonium salt is polyhexamethylene biguanide, polyhexamethylene biguanide is preferably not comprised in an amount of no less than 0.5% (w/v) (the content is less than 0.5% (w/v)), more preferably not comprised in an amount of no less than 0.10% (w/v) (the content is less than 0.10% (w/v)), still more preferably not comprised in an amount of no less than 0.05% (w/v), yet more preferably not comprised in an amount of no less than 0.01% (w/v), yet still more preferably not comprised in an amount of no less than 0.005% (w/v), even more preferably not comprised in an amount of no less than 0.001% (w/v), yet even more preferably not comprised in an amount of no less than 0.0005% (w/v), and in particular preferably not comprised in an amount of no less than 0.0001% (w/v). Most preferably it is not substantially comprised. Moreover, the antiseptic agent in an embodiment of the present invention refers to a component labelled as an antiseptic agent for a pharmaceutical composition, but does not encompass a component which is itself an active ingredient of a drug in the pharmaceutical composition according to an embodiment of the present invention showing an antiseptic effect, but is not labelled as an antiseptic agent.

The aforementioned antiseptic agents which are preferably not comprised in the pharmaceutical composition according to an embodiment of the present invention or preferably comprised in a predetermined amount comprise benzalkonium chloride, quaternary ammonium salts other than benzalkonium chloride, polyhexamethylene biguanide, and boric acid or a salt thereof. The aforementioned antiseptic agents which are preferably not comprised in the pharmaceutical composition according to an embodiment of the present invention or preferably comprised in a predetermined amount may be used alone or in combination of two or more.

The pharmaceutical composition according to an embodiment of the present invention may also comprise an active ingredient of a drug. Active ingredients can be appropriately selected without particular limitation, depending on the purposes, but they comprise, for example, rebamipide, brimonidine, dorzolamide, brinzolamide, timolol, bunazosin, carteolol, nipradilol, betaxolol, levobunolol, metipranolol, latanoprost, travoprost, bimatoprost, isopropylunoprostone, apraclonidine, or salts thereof. Among these, latanoprost or bimatoprost is a preferred active ingredient. Here, an active ingredient of a drug may itself have an antiseptic effect. However, the pharmaceutical composition according to an embodiment of the present invention, which comprises the aforementioned antiseptic agent (meglumine or a salt thereof), may be suitably used as a pharmaceutical composition comprising an active ingredient other than an active ingredient having an antiseptic effect or an active ingredient showing a small antiseptic effect. Further, the pharmaceutical composition may be those which do not comprise a specific active ingredient, for example, may be those which do not comprise rebamipide, brimonidine, dorzolamide, brinzolamide, timolol, bunazosin, carteolol, nipradilol, betaxolol, levobunolol, metipranolol, latanoprost, travoprost, bimatoprost, isopropylunoprostone, apraclonidine, or salts thereof.

An active ingredient to be comprised in the pharmaceutical composition according to an embodiment of the present invention may be in a form of a salt, and there is no particular limitation for the salt as long as it is a pharmaceutically acceptable salt. Examples of the salt comprise salts of inorganic acids, salts of organic acids, quaternary ammonium salts, salts of halogen ions, salts of alkali metals, salts of alkaline earth metals, metal salts, salts of organic amines, and the like. Salts of inorganic acids comprise salts of hydrochloric acid, hydrobromic acid, hydroiodic acid, nitric acid, sulfuric acid, phosphoric acid, and the like. Salts of organic acids comprise salts of acetic acid, oxalic acid, fumaric acid, maleic acid, succinic acid, malic acid, citric acid, tartaric acid, adipic acid, gluconic acid, glucohept acid, glucuronic acid, terephthalic acid, methanesulfonic acid, alanine, lactic acid, hippuric acid, 1,2-ethanedisulfonic acid, isethionic acid, lactobionic acid, oleic acid, gallic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid, sulfosalicylic acid, and the like. Quaternary ammonium salts comprise salts of methyl bromide, methyl iodide, and the like. Salts of halogen ions comprise salts of chloride ions, bromide ions, iodide ions, and the like. Salts of alkali metals comprise salts of lithium, sodium, potassium, and the like. Salts of alkaline earth metals comprise salts of calcium, magnesium, and the like. Metal salts comprise salts of iron, zinc, and the like. Salts of organic amines comprise salts of triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, N,N-bis(phenylmethyl)-1,2-ethanediamine, and the like.

An active ingredient and a salt thereof to be comprised in the pharmaceutical composition according to an embodiment of the present invention may be in a form of a hydrate or solvate.

An additive other than meglumine may be contained in a pharmaceutical composition which comprises the antiseptic agent according to an embodiment of the present invention, if desired. A surfactant, a buffer agent, a tonicity agent, a stabilizing agent, an anti-oxidative agent, a high molecular weight polymer, and/or the like may be added as an additive.

A surfactant which can be used as an additive for pharmaceutical products, for example, a cationic surfactant, an anionic surfactant, a nonionic surfactant may be formulated in a pharmaceutical composition which comprises the antiseptic agent according to an embodiment of the present invention. Examples of the anionic surfactant comprise phospholipids and the like, and phospholipids comprise lecithin and the like. Examples of the cationic surfactant comprise alkylamine salts, alkylamine polyoxyethylene adducts, fatty acid triethanolamine monoester salts, acylaminoethyldiethylamine salts, fatty acid polyamine condensates, alkylimidazoline, 1-acylaminoethyl-2-alkylimidazoline, 1-hydroxylethyl-2-alkylimidazoline, and the like. Examples of the nonionic surfactant comprise polyoxyethylene fatty acid esters, polyoxyethylene sorbitan fatty acid esters, polyoxyethylene hydrogenated castor oils, polyoxyethylene castor oils, polyoxyethylene polyoxypropylene glycols, sucrose fatty acid esters, vitamin E TPGS, and the like. When a surfactant is formulated in a pharmaceutical composition which comprises the antiseptic agent according to an embodiment of the present invention, the content of the surfactant may be appropriately adjusted depending on the type of the surfactant, and others, but is preferably 0.001 to 10% (w/v), more preferably 0.01 to 5% (w/v), still more preferably 0.1 to 3% (w/v), and most preferably 0.2 to 2% (w/v).

Polyoxyethylene fatty acid esters comprise polyoxyl 40 stearate and the like.

Polyoxyethylene sorbitan fatty acid esters comprise polysorbate 80, polysorbate 60, polysorbate 40, polyoxyethylene sorbitan monolaurate, polyoxyethylene sorbitan trioleate, polysorbate 65, and the like. Polysorbate 80 is particularly preferred.

As polyoxyethylene hydrogenated castor oils, various polyoxyethylene hydrogenated castor oils having different numbers of polymerized ethyleneoxides may be used. The number of polymerized ethyleneoxides is preferably 10 to 100, more preferably 20 to 80, in particular preferably 40 to 70, and most preferably 60. Specific examples of polyoxyethylene hydrogenated castor oils comprise polyoxyethylene hydrogenated castor oil 10, polyoxyethylene hydrogenated castor oil 40, polyoxyethylene hydrogenated castor oil 50, polyoxyethylene hydrogenated castor oil 60, and the like.

As polyoxyethylene castor oils, various polyoxyethylene castor oils having different numbers of polymerized ethyleneoxides may be used. The number of polymerized ethyleneoxides is preferably 5 to 100, more preferably 20 to 50, in particular preferably 30 to 40, and most preferably 35. Specific examples of polyoxyethylene castor oils comprise polyoxyl 5 castor oil, polyoxyl 9 castor oil, polyoxyl 15 castor oil, polyoxyl 35 castor oil, polyoxyl 40 castor oil, and the like.

Polyoxyethylene polyoxypropylene glycols comprise polyoxyethylene (160) polyoxypropylene (30) glycol, polyoxyethylene (42) polyoxypropylene (67) glycol, polyoxyethylene (54) polyoxypropylene (39) glycol, polyoxyethylene (196) polyoxypropylene (67) glycol, polyoxyethylene (20) polyoxypropylene (20) glycol, and the like.

Sucrose fatty acid esters comprise sucrose stearate, and the like.

Vitamin E TPGS is also referred to as tocopherol polyethylene glycol 1000 succinate.

A buffer agent which can be used as an additive for pharmaceutical products may be formulated in a pharmaceutical composition which comprises the antiseptic agent according to an embodiment of the present invention. Examples of a buffer agent other than meglumine comprise phosphoric acid or a salt thereof, citric acid or a salt thereof, acetic acid or a salt thereof, carbonic acid or a salt thereof, tartaric acid or a salt thereof, ε-aminocaproic acid, trometamol, and the like. ε-aminocaproic acid is particularly preferred. Phosphates comprise sodium phosphate, sodium dihydrogen phosphate, disodium hydrogen phosphate, potassium phosphate, potassium dihydrogen phosphate, dipotassium hydrogen phosphate, and the like. Citrates comprise sodium citrate, disodium citrate, and the like. Acetates comprise sodium acetate, potassium acetate, and the like. Carbonates comprise sodium carbonate, sodium hydrogen carbonate, and the like. Tartrates comprise sodium tartrate, potassium tartrate, and the like. When a buffer agent is formulated in a pharmaceutical composition which comprises the antiseptic agent according to an embodiment of the present invention, the content of a buffer agent other than meglumine may be appropriately adjusted depending on the type of the buffer agent, and others, but is preferably 0.001 to 10% (w/v), more preferably 0.01 to 5% (w/v), still more preferably 0.1 to 3% (w/v), and most preferably 0.2 to 2% (w/v).

A tonicity agent which can be used as an additive for pharmaceutical products may be appropriately formulated in a pharmaceutical composition which comprises the antiseptic agent according to an embodiment of the present invention. Examples of the tonicity agent comprise ionic tonicity agents, nonionic tonicity agents, and the like. Ionic tonicity agents comprise sodium chloride, potassium chloride, calcium chloride, magnesium chloride, and the like. Nonionic tonicity agents comprise glycerin, propylene glycol, sorbitol, mannitol, and the like. When a tonicity agent is formulated in a pharmaceutical composition according to an embodiment of the present invention, the content of the tonicity agent may be appropriately adjusted depending on the type of the tonicity agent, and others, but is preferably 0.01 to 10% (w/v), more preferably 0.1 to 5% (w/v), and most preferably 0.5 to 3% (w/v).

A stabilizing agent which can be used as an additive for pharmaceutical products may be appropriately formulated in a pharmaceutical composition which comprises the antiseptic agent according to an embodiment of the present invention. Examples of a stabilizing agent other than meglumine comprise edetic acid, monosodium edetate, disodium edetate, tetrasodium edetate, sodium citrate, and the like. Disodium edetate is preferred, and disodium edetate dihydrate is particularly preferred. When a stabilizing agent is formulated in a pharmaceutical composition according to an embodiment of the present invention, the content of a stabilizing agent other than meglumine may be appropriately adjusted depending on the type of the stabilizing agent, and others, but is preferably 0.0001 to 0.5% (w/v), more preferably 0.0005 to 0.3% (w/v), still more preferably 0.001 to 0.1% (w/v), yet more preferably 0.002 to 0.08% (w/v), yet still more preferably 0.003 to 0.07% (w/v), in particular preferably 0.005 to 0.06% (w/v), and most preferably 0.007 to 0.05% (w/v).

An anti-oxidative agent which can be used as an additive for pharmaceutical products may be appropriately formulated in a pharmaceutical composition which comprises the antiseptic agent according to an embodiment of the present invention. Examples of the anti-oxidative agent comprise ascorbic acid, tocopherol, dibutylhydroxytoluene, butylhydroxyanisol, sodium erythorbate, propyl gallate, sodium sulfite, and the like. When an anti-oxidative agent is formulated in a pharmaceutical composition according to an embodiment of the present invention, the content of the anti-oxidative agent may be appropriately adjusted depending on the type of the anti-oxidative agent, and others, but is preferably 0.0001 to 1% (w/v), more preferably 0.001 to 0.1% (w/v), and most preferably 0.005 to 0.010% (w/v).

A high molecular weight polymer which can be used as an additive for pharmaceutical products may be appropriately formulated in a pharmaceutical composition which comprises the antiseptic agent according to an embodiment of the present invention. Examples of the high molecular weight polymer comprise methylcellulose, ethylcellulose, hydroxymethylcellulose, hydroxyethylcellulose, hydroxypropylcellulose, hydroxyethylmethylcellulose, hydroxypropylmethylcellulose, carboxymethylcellulose, carboxymethylcellulose sodium, hydroxypropylmethylcellulose acetate succinate, hydroxypropylmethylcellulose phthalate, carboxymethylethylcellulose, cellulose acetate phthalate, polyvinylpyrrolidone, polyvinyl alcohol, carboxyvinyl polymer, polyethylene glycol, and the like. When a high molecular weight polymer is formulated in a pharmaceutical composition according to an embodiment of the present invention, the content of the high molecular weight polymer may be appropriately adjusted depending on the type of the high molecular weight polymer, and others, but is preferably 0.001 to 5% (w/v), more preferably 0.01 to 3% (w/v), and most preferably 0.1 to 1% (w/v).

A pH adjuster which can be used as an additive for pharmaceutical products may be appropriately formulated in a pharmaceutical composition which comprises the antiseptic agent according to an embodiment of the present invention. Examples of pH adjusters other than meglumine comprise hydrochloric acid, phosphoric acid, citric acid, acetic acid, sodium hydroxide, potassium hydroxide, sodium carbonate, sodium hydrogen carbonate, and the like.

The pH of a pharmaceutical composition which comprises the antiseptic agent according to an embodiment of the present invention is preferably 4.0 to 9.5, more preferably 5.0 to 9.0, still more preferably 5.5 to 8.8, yet still more preferably 6.0 to 8.7, in particular preferably 6.5 to 8.6, and most preferably 7.0 to 8.5.

A pharmaceutical composition which comprises the antiseptic agent according to an embodiment of the present invention is preferably placed in a repeatedly operable container. Examples of the repeatedly operable container comprise a multi-dose container, a recappable unit dose container, and the like. The multi-dose container is configured such that a cap and the like can be freely opened and closed for the purpose of using it multiple times. However, a PFMD (Preservative Free Multi Dose) container which has a special structure for achieving an antiseptic effect such as a backflow prevention mechanism is not encompassed. The recappable unit dose container can be repeatedly used by recapping. There is no particular limitation for the material of the container, but, for example, containers made of polyethylene (PE), polypropylene (PP), and polyethylene terephthalate (PET), or the like can be used.

There is no particular limitation for the dosage form of a pharmaceutical composition which comprises the antiseptic agent according to an embodiment of the present invention as long as it can be used as a pharmaceutical product, but it is preferably an eye drop, and can be manufactured in accordance with a conventional method in the art.

The pharmaceutical composition according to an embodiment of the present invention is useful for contact lenses (wearing persons). There is no particular limitation for the types of contact lenses to be applied, but examples thereof comprise hard contact lenses, soft contact lenses, and the like. They may be oxygen-permeable contact lenses. Soft contact lenses comprise hydrous soft contact lenses, non-hydrous soft contact lenses, (nonionic) silicone hydrogel soft contact lenses, and the like.

Detailed descriptions of the aforementioned antiseptic agent according to an embodiment of the present invention and a pharmaceutical composition which comprises the antiseptic agent according to an embodiment of the present invention can also be used for a product comprising the pharmaceutical composition according to an embodiment of the present invention and a repeatedly operable container (for storing the pharmaceutical composition) and a method of improving an antiseptic effect.

<Method of Improving Antiseptic Effect>

The method of improving an antiseptic effect according to an embodiment of the present invention is preferably a method of improving an antiseptic effect of a pharmaceutical composition, the method comprising further comprising meglumine or a salt thereof in the pharmaceutical composition placed in a repeatedly operable container.

The method of improving an antiseptic effect according to an embodiment of the present invention is preferably a method of improving an antiseptic effect, the method further comprising meglumine or a salt thereof in a pharmaceutical composition comprising no or a predetermined amount of an antiseptic agent, the pharmaceutical composition being placed in a repeatedly operable container. Here, the terms "antiseptic agent" and "predetermined amount" as used in the method of improving an antiseptic effect according to an embodiment of the present invention may have similar meanings as described with regard to the antiseptic agent according to an embodiment of the present invention and the pharmaceutical composition according to an embodiment of the present invention. In particular, antiseptic agents which are preferably not comprised in a pharmaceutical composition or antiseptic agents which are preferably comprised in a predetermined amount are polyhexamethylene biguanide, boric acid and a salt thereof, benzalkonium chloride, and quaternary ammonium salts other than benzalkonium chloride. Among these, antiseptic agents which are preferably not comprised or antiseptic agents which are preferably comprised in a predetermined amount may be used alone or in combination of two or more.

For a pharmaceutical composition before adding meglumine or a salt thereof in the method of improving an antiseptic effect according to an embodiment of the present invention, the common logarithmic value of the ratio (B/A) of a cell count (B) to a cell count (A) is preferably 3.3 or less, more preferably 3.0 or less, still more preferably 2.8 or less, in particular preferably 2.5 or less, and most preferably 2.0 or less, the cell count (A) being a viable cell count as measured by inoculating and uniformly mixing the pharmaceutical composition with *Escherichia coli* ATCC 8739 at a microorganism liquid concentration within a range of between $10^5$ and $10^6$ cfu/mL, storing the pharmaceutical composition at 20 to 25° C. under a light shielding condition for 14 days, and then withdrawing 1 mL of the pharmaceutical composition with a micropipette to measure the viable cell count, and the cell count (B) being at the time of the inoculation.

For a pharmaceutical composition after adding meglumine or a salt thereof as mentioned above in the method of improving an antiseptic effect according to an embodiment of the present invention, the common logarithmic value of the ratio (B/A) of a cell count (B) to a cell count (A) is preferably 2.9 or more, more preferably 3.0 or more, still more preferably 3.4 or more, yet more preferably 3.5 or more, and most preferably 4.0 or more, the cell count (A) being a viable cell count as measured by inoculating and uniformly mixing the pharmaceutical composition with *Escherichia coli* ATCC 8739 at a microorganism liquid concentration within a range of between $10^5$ and $10^6$ cfu/mL, storing the pharmaceutical composition at 20 to 25° C. under a light shielding condition for 14 days, and then withdrawing 1 mL of the pharmaceutical composition with a micropipette to measure the viable cell count, and the cell count (B) being at the time of the inoculation. Alternatively, in the method of improving an antiseptic effect according to an embodiment of the present invention, a pharmaceutical composition after adding dorzolamide or a salt thereof as mentioned above preferably satisfies the standard of "category IA" according to the informative "Preservatives-Effectiveness Tests" defined in The Japanese Pharmacopoeia, 16th edition.

EXAMPLES

Below, Formulation Examples and results from antisepsis effectiveness tests will be shown. These are intended for better understanding of the present invention, but not for limiting the scope of the present invention.

Formulation Examples

Below, typical Formulation Examples of the present invention will be shown. It is noted that the formulated amounts of components in the following Formulation Examples are each expressed in terms of a content per mL of a formulation.

Formulation Example 1 (in a Multi-Dose Container)

Meglumine: 10 mg
Dilute hydrochloric acid: q.s. Sodium hydroxide: q.s.
Purified water: q.s.

Formulation Example 2 (in a Multi-Dose Container)

Meglumine: 20 mg
Dilute hydrochloric acid: q.s. Sodium hydroxide: q.s.
Purified water: q.s.

It is noted that the types and/or formulated amounts of meglumine and the additives in the above Formulation Examples 1 and 2 may be appropriately adjusted to obtain desired compositions.

Antisepsis Effectiveness Tests

1. Preparation of Test Formulations

Polysorbate 80 (1 g), meglumine (5 g), boric acid (0.6 g), and disodium edetate dihydrate (0.05 g) were dissolved in water, and adjusted to pH 8.3 with a pH regulator. Water was then added to a total volume of 100 mL. The resulting liquid was sterile filtered to prepare a formulation of Example 1. Examples 2 to 11 and Comparative Example 1 were prepared as in Example 1 except that the components, addition amounts, pH, and the like were altered according to the formulations shown in Tables 1 to 3 below.

2. Test Method

The following strains were used as inoculum strains.

Bacteria:

*Escherichia coli* ATCC 8739 (may also be referred to as *E. coli*)

*Pseudomonas aeruginosa* ATCC 9027 (may also be referred to as *P. aeruginosa*)

*Staphylococcus aureus* ATCC 6538 (may also be referred to as *S. aureus*)

Yeast and molds:

*Candida albicans* ATCC 10231 (may also be referred to as *C. albicans*)

*Aspergillus brasiliensis* ATCC16404 (may also be referred to as *A. brasiliensis*)

A test sample of each formulation was inoculated with an inoculum microorganism liquid so that the concentration of the microorganism liquid in the test sample was $10^5$ to $10^6$ cells/mL (for each of the 5 strains). Specifically, an inoculum microorganism liquid was prepared for each strain at $10^7$ to $10^8$ cfu/mL, and inoculated into a test sample of each of Examples 1 to 11 and Comparative Example 1, and uniformly mixed to obtain a sample, so that the inoculum microorganism liquid was at $10^5$ to $10^6$ cfu/mL. These samples were stored at 20 to 25° C. under a light shielding condition. At sampling points (after 14 days or 28 days), 1 mL of each sample was withdrawn with a micropipette to measure a viable cell count. At each sampling point, the following operation was performed: a lid for a sample solution was opened, and then sampling was performed, and the lid was then closed.

3. Test Results and Discussion

Test results are shown in Tables 1 to 3. The test results in Tables 1 to 3 are each shown as the common logarithm value of the ratio (B/A) of a cell count (B) at the time of inoculation to a cell count (A) of viable cells. For example, the value "1" means that the measured viable cell count is as low as 10% of the inoculum cell count. Further, the formulations were evaluated whether they satisfied the standard of "category IA" according to the informative "Preservatives-Effectiveness Tests" defined in The Japanese Pharmacopoeia, 16th edition.

TABLE 1

| % Component(w/v) | Example 1 | Example 2 | Example 3 | Example 4 | Example 5 |
|---|---|---|---|---|---|
| Meglumine | 5 | 5 | 5 | 5 | 5 |
| Polysorbate 80 | 1 | 1 | — | 1 | 1 |
| Boric acid | 0.6 | 0.6 | — | 0.6 | — |
| Disodium edetate dihydrate | 0.05 | 0.05 | — | — | 0.01 |
| Benzalkonium chloride | — | 0.008 | — | — | — |
| Dilute hydrochloric acid | q.s. | q.s. | q.s. | q.s. | q.s. |
| Purified water | q.s. | q.s. | q.s. | q.s. | q.s. |
| pH | 8.3 | 8.3 | 8.3 | 8.3 | 8.3 |

| Antisepsis effectiveness tests | | | | | | |
|---|---|---|---|---|---|---|
| Strain | Sampling | \multicolumn{5}{c}{Results (logarithmic decrement)} | | | | |
| *E. coli* | 14 d | >4.4 | >4.4 | >4.3 | 3.4 | >4.3 |
| | 28 d | >4.4 | >4.4 | >4.3 | >4.3 | >4.3 |
| *P. aeruginosa* | 14 d | >4.6 | >4.6 | >4.9 | >4.9 | >4.9 |
| | 28 d | >4.6 | >4.6 | >4.9 | >4.9 | >4.9 |
| *S. aureus* | 14 d | >5.0 | >4.0 | >5.2 | >5.2 | >5.2 |
| | 28 d | >5.0 | >4.0 | >5.2 | >5.2 | >5.2 |
| *C. albicans* | 14 d | 3.9 | >4.5 | 3.5 | >4.7 | >4.7 |
| | 28 d | >4.5 | >4.5 | >4.7 | >4.7 | >4.7 |
| *A. brasiliensis* | 14 d | 0.3 | 1.4 | 0.3 | 0.5 | 0.3 |
| | 28 d | −0.1 | 2.9 | 0.7 | 0.9 | 1.0 |
| Evaluation | | Satisfied | Satisfied | Satisfied | Satisfied | Satisfied |

TABLE 2

| % Component(w/v) | Example 6 | Example 7 | Example 8 | Comparative Example 1 |
|---|---|---|---|---|
| Meglumine | 5 | 5 | 5 | — |
| Polysorbate 80 | 1 | 1 | — | 1 |
| Boric acid | 0.6 | 0.6 | 0.6 | 0.6 |
| Disodium edetate dihydrate | 0.01 | 0.01 | 0.01 | 0.05 |
| Dilute hydrochloric acid | q.s. | q.s. | q.s. | q.s. |
| Purified water | q.s. | q.s. | q.s. | q.s. |
| pH | 7 | 8.3 | 8.3 | 8.3 |

TABLE 2-continued

| % Component(w/v) | | Example 6 | Example 7 | Example 8 | Comparative Example 1 |
|---|---|---|---|---|---|
| Antisepsis effectiveness tests | | | | | |
| Strain | Sampling | Results (logarithmic decrement) | | | |
| E. coli | 14 d | >4.3 | >4.3 | >4.3 | 2.8 |
| | 28 d | >4.3 | >4.3 | >4.3 | >4.4 |
| P. aeruginosa | 14 d | >4.9 | >4.9 | >4.9 | >4.6 |
| | 28 d | >4.9 | >4.9 | >4.9 | >4.6 |
| S. aureus | 14 d | 4.3 | >5.2 | 4.8 | 4.5 |
| | 28 d | >5.2 | >5.2 | >5.2 | >5.0 |
| C. albicans | 14 d | >4.7 | 4.1 | 4.7 | 4.1 |
| | 28 d | >4.7 | >4.7 | >4.7 | >4.5 |
| A. brasiliensis | 14 d | 0.7 | 0.9 | 0.7 | 1.1 |
| | 28 d | 0.5 | 0.5 | 0.7 | 1.5 |
| Evaluation | | Satisfied | Satisfied | Satisfied | Satisfied |

TABLE 3

| % Component(w/v) | | Example 9 | Example 10 | Example 11 |
|---|---|---|---|---|
| Bimatoprost | | 0.03 | 0.03 | — |
| Latanoprost | | — | — | 0.005 |
| Meglumine | | 5 | 3 | 3 |
| Boric acid | | 0.6 | — | — |
| ε-aminocaproic acid | | — | — | 0.2 |
| Polysorbate 80 | | — | — | 0.1 |
| Disodium edetate dihydrate | | 0.01 | 0.01 | 0.02 |
| Dilute hydrochloric acid/sodium hydroxide | | q.s. | q.s. | q.s. |
| Purified water | | q.s. | q.s. | q.s. |
| PH | | 7.0 | 7.0 | 6.0 |
| Antisepsis effectiveness tests | | | | |
| Strain | Sampling | Results (logarithmic decrement) | | |
| E. coli | 14 d | >4.6 | >4.6 | >4.7 |
| | 28 d | >4.6 | >4.6 | >4.7 |
| P. aeruginosa | 14 d | >4.5 | >4.5 | >4.6 |
| | 28 d | >4.5 | >4.5 | >4.6 |
| S. aureus | 14 d | 3.1 | 4.1 | >4.8 |
| | 28 d | >5.0 | >5.0 | >4.8 |
| C. albicans | 14 d | 2.8 | 3.6 | 0.1 |
| | 28 d | 4.4 | 4.0 | 1.0 |
| A. brasiliensis | 14 d | 0.4 | 0.4 | 0.5 |
| | 28 d | 0.5 | 0.5 | 0.5 |
| Evaluation | | Satisfied | Satisfied | Satisfied |

As shown in Tables 1 to 3, the formulations from Examples 1 to 11 containing meglumine demonstrated an antiseptic effect against each of the strains, and satisfied the standard of "category IA" according to the informative "Preservatives-Effectiveness Tests" defined in The Japanese Pharmacopoeia, 16th edition. In contrast, the formulation from Comparative Example 1 which did not contain meglumine showed an inferior antiseptic effect, and did not satisfy the standard. These results revealed that meglumine alone has an antiseptic effect.

The invention claimed is:

1. A product comprising an eye drop composition, and a repeatedly operable container, wherein
   the eye drop composition comprises meglumine or a salt thereof, and an active ingredient of a drug, and
   the eye drop composition does not comprise an antiseptic agent other than meglumine and a salt thereof,
   the active ingredient is an active ingredient other than an active ingredient having an antiseptic effect, and
   the repeatedly operable container does not comprise a multi dose container equipped with a structure for achieving an antiseptic effect.

2. The product according to claim 1, having a content of meglumine or a salt thereof of 0.1 to 20% (w/v) in the eye drop composition.

3. The product according to claim 1, having a pH of 4.0 to 9.5 of the eye drop composition.

* * * * *